(12) United States Patent
Sas et al.

(10) Patent No.: US 7,101,908 B2
(45) Date of Patent: Sep. 5, 2006

(54) BICYCLIC CARBOHYDRATE COMPOUNDS USEFUL IN THE TREATMENT OF INFECTIONS CAUSED BY HERPESVIRIDAE

(75) Inventors: Benedikt Sas, Stekene (BE); Johan Van Hemel, Antwerp (BE); Jan Vandenkerckhove, Zichem (BE); Eric Peys, Balen (BE); Johan van der Eycken, Ninove (BE); Bart Ruttens, Ghent (BE); Petra Blom, Sint-Amandsberg (BE)

(73) Assignee: Kemin Pharma Europe B.V.B.A., Des Moines, IA (US)

( * ) Notice: Subject to any disclaimer, the term of this patent is extended or adjusted under 35 U.S.C. 154(b) by 28 days.

(21) Appl. No.: 10/690,914

(22) Filed: Oct. 22, 2003

(65) Prior Publication Data

Related U.S. Application Data

(63) Continuation-in-part of application No. 09/977,478, filed on Oct. 15, 2001.

(51) Int. Cl.
*A61K 31/357* (2006.01)
*C07D 493/04* (2006.01)

(52) U.S. Cl. ..................... 514/452; 549/364
(58) Field of Classification Search ............. 549/396, 549/364; 514/456, 452
See application file for complete search history.

(56) References Cited

FOREIGN PATENT DOCUMENTS

WO WO 03/032905 A2 * 4/2003

OTHER PUBLICATIONS

Database CAPLUS on STN, AN 2001:544756. Espinola et al. "Synthetic Flux-Promoting Polyether Modesl: Cation Flux Dependence on Polyoxyethylene Chain Length", Isreal Journal of Chemistry. 2000, vol. 40, Issue 3-4.

* cited by examiner

*Primary Examiner*—Bernard Dentz
(74) *Attorney, Agent, or Firm*—Kent A. Herink; Daniel A. Rosenberg; Emily E. Harris

(57) ABSTRACT

Bicyclic carbohydrates for the treatment of infections caused by herpseviridae, and in particular cytomegalovirus. The invention consists of the novel bicyclic carbohydrates the generic structure of which is:

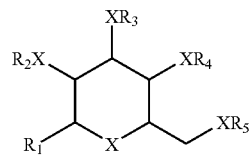

wherein $R_1$ is either -Bn or -Ph; $R_2$ and $R_3$ are either -alkyl, -aryl, -allyl, or —H; $R_4$ and $R_5$ form a ring and are either —CH(Ph)- or —CH(aryl)- and X is either O, N or S.

8 Claims, 5 Drawing Sheets

BICYCLIC CARBOHYDRATE COMPOUNDS USEFUL IN THE TREATMENT OF INFECTIONS CAUSED BY HERPESVIRIDAE

This application is a continuation-in-part of co-pending U.S. application Ser. No. 09/977,478, filed Oct. 15, 2001.

BACKGROUND OF THE INVENTION

The invention relates generally to compounds active against viral diseases and, more specifically to bicyclic carbohydrate compounds that are useful in the prophylaxis and treatment of diseases caused by the alphaherpesvirina cytomegalovirus.

Cytomegalovirus (CMV) is the largest human herpes virus, and there is only one serotype. As with animal CMVs it is species specific; humans are the natural hosts and animal CMVs do not infect humans. The name refers to the multinucleated cells, which together with the intranuclear inclusions, are characteristic responses to infection with this virus. Transmission is via saliva, and CMVs were originally called 'salivary gland' viruses. Urine is an additional source of infection in children, and in infected pregnant women the virus can spread via the blood to the placenta and fetus. Semen and cervical secretions may also contain virus and it can therefore be spread by sexual contact. It is often present in milk in small quantities, but this is of doubtful significance in transmission. In hospitals it can be transmitted by blood transfusion and organ transplants. CMV infections are often asymptomatic, but can reactivate and cause disease when CMI (cell mediated immune response) defenses are impaired. After clinical silent infection of unknown cells in the upper respiratory tract, CMV spreads locally to lymphoid tissues and then systemically in circulating lymphocytes and monocytes to involve lymph nodes and the spleen. The infection then localizes in epithelial cells in salivary glands and kidney tubules, and in cervix, testes and epididymis, from where the virus is shed to the outside world (Table 1).

TABLE 1

Cytomegalovirus infections

| Site of infection | Result | Comment |
|---|---|---|
| Salivary glands | Salivary transmission | Importance of kissing and contaminated hands |
| Tubular epithelium of kidney | Virus in urine | Probable role of transmission |
| Cervix/Testis/epididymis | Sexual transmission | Up to $10^7$ infectious doses/ml of semen in an acutely infected male |
| Lymphocytes/Macrophages | Virus spread through body via infected cells Mononucleosis may occur Immunosuppressive effect | Probable site of persistent infection |
| Placenta/Fetus | Congenital abnormalities | Greatest damage in fetus after primary maternal infection rather than reactivation |

Infected cells may be multinucleated or bear intranuclear inclusions, but pathologic changes are minor and infection is generally asymptomatic. In young adults, a glandular fever type illness can occur, but without heterophil antibodies. There is fever and lethargy, and abnormal lymphocytes and mononucleosis in blood smears. The virus inhibits T cell responses and there is a temporary reduction in their immune reactivity to other antigens. Although specific antibodies and CMI responses are generated, these fail to clear the virus, which often continues to be shed in saliva and urine for many months. The infection is, however, eventually controlled by CMI mechanisms, although infected cells remain in the body throughout life and can be a source of reactivation and disease when CMI defenses are impaired. CMV owes its success in our species to its ability to evade immune defenses (Cann A. J. (1997) Principles of Molecular Virology. Second Edition. Academic Press, San Diego, pp. 65–67; Mims C., Playfair J., Roitt I., Wakelin D. and Williams R. (1998) Medicinal Microbiology. Second Edition. Mosby International Limited, pp.347–348).

Ganciclovir is an anti-CMV drug that works by inhibiting CMV's DNA polymerase enzyme. It can prevent CMV from reproducing and infecting new cells, but it cannot eliminate it from the body. Ganciclovir is manufactured by Roche under the trade name Cymevene. In the US its trade name is Cytovene. Ganciclovir now comes in several formulations: oral, intravenous and intravitreal (into the eye). It is either given intravenously on a long-term basis through a catheter or in a pill form. In the case of administration by catheter, one end of a tube is surgically inserted into a large vein in the chest, the other end of the tube remains outside the chest or has an injectable port just under the skin. Although slightly less efficient, an oral form of ganciclovir is also approved by the FDA for prevention and maintenance treatment of CMV.

Unfortunately, ganciclovir also suppresses bone-marrow production of the white blood cells called neutrophils. This condition is called neutropenia. People taking ganciclovir require close monitoring to ensure blood disorders are promptly detected. It can also harm the kidneys, reduce testosterone levels, and cause nausea, vomiting, diarrhea and rash. More than 10% of IV ganciclovir recipients have to stop treatment because of these side effects. In addition, the development of strains of CMV that are resistant to ganciclovir has been reported. These do not seem to develop any faster with oral ganciclovir than with the intravenous formulation (www.aidsmap.com).

Alternative compounds with activity against herpes viruses such as cytomegalovirus are needed.

SUMMARY OF THE INVENTION

The invention consists of the novel bicyclic carbohydrates the generic structure of which is:

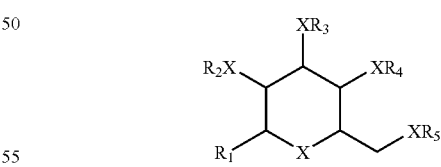

wherein $R_1$ is either -Bn or -Ph; $R_2$ and $R_3$ are either -alkyl, -aryl, -allyl, or —H; $R_4$ and $R_5$ form a ring and are either —CH(Ph)- or —CH(aryl)- and X is either O, N or S, herein referred to as Formula A. Compounds of Formula A have activity against infections caused by the cytomegalovirus. The invention also includes analogs, prodrugs and pharmaceutically acceptable salts thereof, together with pharmaceutical compositions for the prophylaxis and treatment of diseases caused by infections of alphaherpesvirinae and particularly cytomegalovirus.

DETAILED DESCRIPTION OF A PREFERRED EMBODIMENT

Figure 1:
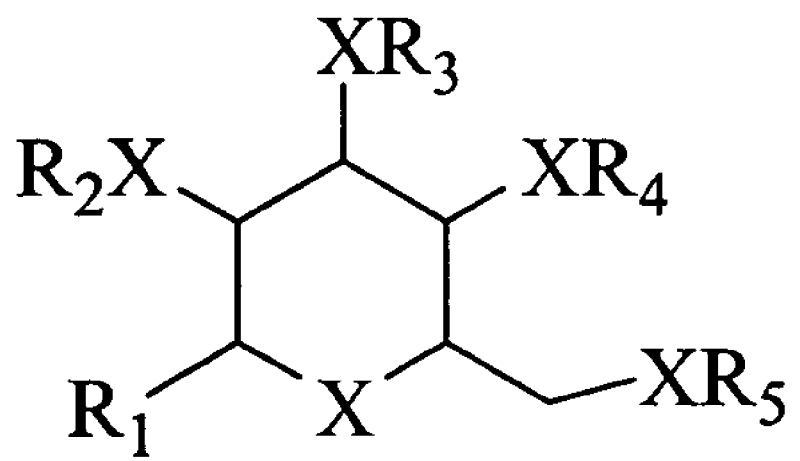
FIG. 1 is a chemical structure of the bicyclic carbohydrates of the present invention and designated Formula A.
Figure 2:
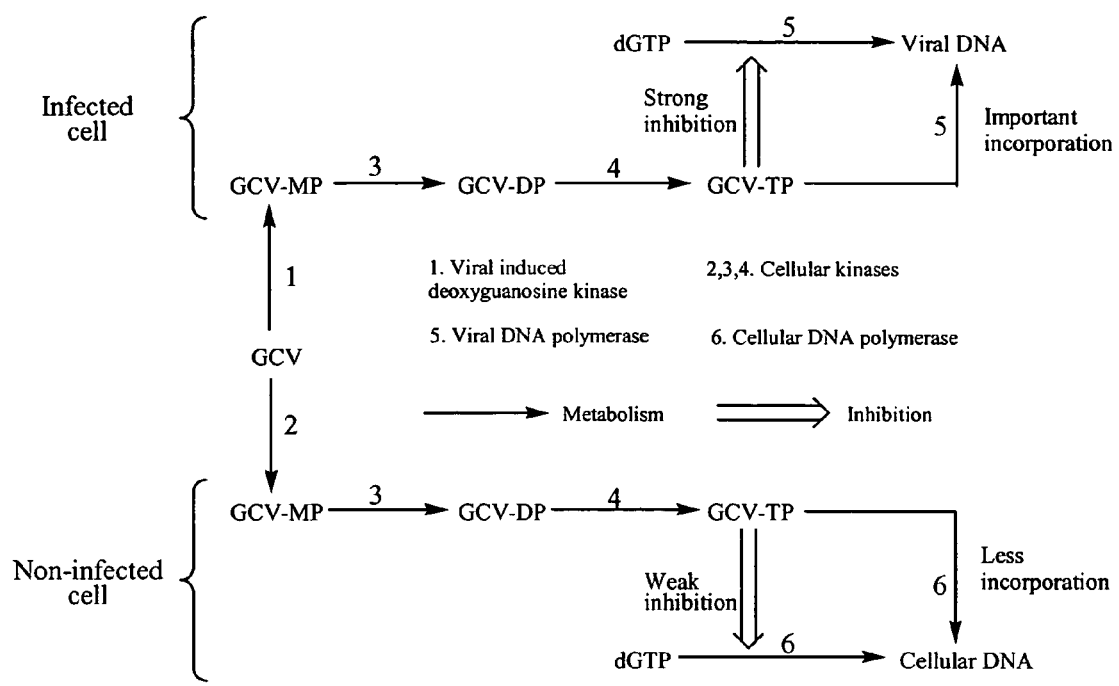
FIG. 2 is a diagrammatic representation of the activity of ganciclovir in cells that are non-infected and cells that are infected with herpes virus.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, acetate ascorbate, benzoate, citrate, etoglutarate, glycerophosphate, malonate, methanesulfonate, succinate, and tartarate. Suitable inorganic salts may also be formed, including bicarbonate, carbonate, hydrochloride, nitrate, and sulfate, salts.

Compounds of the present invention can conveniently be administered in a pharmaceutical composition containing the compound in combination with a suitable excipient, the composition being useful in combating viral infections. Depending on whether the preparation is used to treat internal or external viral infections, the compounds and compositions of the present invention can be administered parenterally, topically, intravaginally, orally, or rectally.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity. Methods for the extrapolation of effective dosages to humans are known to the art.

The compound is conveniently administered in unit dosage form; for example, containing 0.1 to 2000 mg, conveniently 100 to 1000 mg, most conveniently, 100 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 1 to 30 mg/kg, preferably 1 to 30 mg/kg of mammal body weight, and can be used in man in a unit dosage form, administered one to four times daily in the amount of 1 to 10 mg per unit dose.

For parenteral administration or for administration as drops, as for eye infections, the compounds are presented in aqueous solution in a concentration of from about 0.1 to about 20%, more preferably about 1 to about 5%. The solution may contain other ingredients, such as emulsifiers, antioxidants or buffers.

The exact regimen for administration of the compound and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Compounds of Formula A and pharmaceutically acceptable salts thereof are useful as antiviral agents. Thus, they are useful to combat viral infections in animals, including man. The compounds are generally active against herpes viruses, and are particularly useful in the prophylaxis and treatment of diseases caused by the alphaherpesvirinae cytomegalovirus.

Methods and Materials

The structures of the bicyclic carbohydrates synthesized are presented in Table 2.

TABLE 2

Structures of active compounds

| Compound | Structure | $R_1$ | $R_2$ | $R_3$ | $R_4$ | $R_5$ |
|---|---|---|---|---|---|---|
| Compound A1 | (structure with OMe, MeO, Ph, O, Ph) | —Ph | —OMe | —OMe | —OCH(Ph)OCH$_2$— | |
| Compound A2 | (structure with OMe, MeO, Ph, O, Bn) | —Bn | —OMe | —OMe | —OCH(Ph)OCH$_2$— | |

TABLE 2-continued

Structures of active compounds

| Compound | Structure | R₁ | R₂ | R₃ | R₄ | R₅ |
|---|---|---|---|---|---|---|
| Compound A3 | (pyranose with OEt, EtO, Bn, O-CH(Ph)-O ring) | —Bn | —OEt | —OEt | | —OCH(Ph)OCH₂— |
| Compound A4 | (pyranose with OAll, AllO, Bn, O-CH(Ph)-O ring) | —Bn | —OAll | —OAll | | —OCH(Ph)OCH₂— |
| Compound A5 | (pyranose with OCH₂C≡CH groups, Bn, O-CH(Ph)-O ring) | —Bn | —OCH₂CCH | —OCH₂CCH | | —OCH(Ph)OCH₂— |
| Compound A6 | (pyranose with OMe, MeO, Ph, O-CH(naphthyl)-O ring) | —Ph | —OMe | —OMe | (naphthyl) | —OCHOCH₂— |
| Compound A7 | (pyranose with OMe, MeO, Ph, O-CH(biphenyl)-O ring) | —Ph | —OMe | —OMe | (4-Ph-phenyl) | —OCHOCH₂— |

EXAMPLE 1

Synthesis of the Compounds of Formula A

The compounds were synthesized as follows:

1. Synthesis of Compound A1

Figure 3:
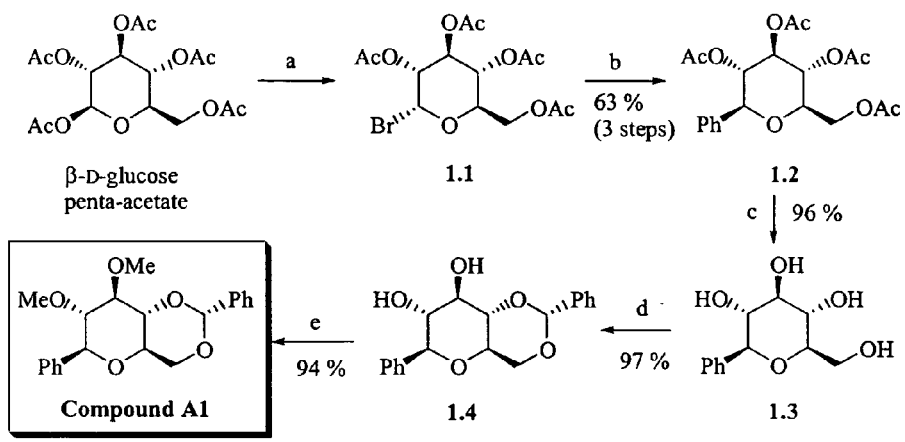
FIG. 3 is a diagrammatic representation of the scheme of synthesis of Compound A1.

The scheme of the synthesis of Compound A1 is illustrated in FIG. 3.

Synthesis of Compound 1.1

To (β)-D-glucose penta-acetate (24.6 g, 63.0 mmol) was added a solution of hydrogen bromide in acetic acid (33 wt %, 100 ml). A dark brown color immediately appears. The reaction mixture was stirred at room temperature for 30 minutes under argon atmosphere. Subsequently the solvent was removed by azeotropic distillation in vacuo with toluene (4×50 ml), yielding a green-brown solid Compound 1.1. The crude product was used in the next reaction step without further purification.

Formula: $C_{14}H_{19}O_9Br$

Molecular weight: 411.20

$R_f$: 0.46 (cyclohexane/ethyl acetate 1:1)

IR (KBr): 2962, 2360, 2342, 1748, 1435, 1369, 1218, 1162, 1112, 1079, 1042, 911, 752, 668, 601, 563 cm$^{-1}$

ES-MS: 433=[410+Na]$^+$, 435=[412+Na$^+$]

$^1$H-NMR (500 MHz, CDCl$_3$): δ 6.61 (1H, d, J=4.0 Hz), 5.56 (1H, dd, app. t, J=9.7 Hz), 5.16 (1H, dd, app. t, J=9.7 Hz), 4.84 (1H, dd, J=10.0, 4.0 Hz), 4.33 (1H, m), 4.30 (1H, m), 4.13 (1H, dd, J=12.3, 1.5 Hz), 2.11 (3H, s), 2.10 (3H, s), 2.05 (3H, s), 2.03 (3H, s)

$^{13}$C-NMR (125 MHz, CDCl$_3$): δ 170.37, 169.70, 169.64, 169.31, 86.34, 71.91, 70.39, 69.94, 66.94, 60.76, 20.48, 20.48, 20.38, 20.38

Synthesis of Compound 1.2

To a solution of phenylmagnesium bromide (200 ml of a 3M solution in diethyl ether, 600 mmol, 9.5 eq) in dry diethyl ether (500 ml), cooled to 0° C., was added a solution of the bromide Compound 1.1 (63.0 mmol theoretical) in dry diethyl ether (500 ml) by canulation. The reaction mixture was stirred at room temperature under argon-atmosphere for 72 hours. Subsequently the reaction mixture was poured out into water (2000 ml), and acetic acid (200 ml) was added to dissolve the magnesium-salts. The two layers were separated, and the organic layer was washed with water (3×500 ml). The combined aqueous layers were concentrated under reduced pressure to yield a light brown solid residue. This residue was dissolved in pyridine (500 ml). At 0° C. acetic anhydride (340 ml) was added slowly. After adding DMAP (200 mg, 1.64 mmol), stirring was continued for 20 hours at room temperature under argon-atmosphere. Next the reaction mixture was concentrated under reduced pressure, followed by azeotropic distillation with toluene (1×250 ml), and the addition of diethyl ether (3 l). The obtained organic layer was washed with sat. NaHCO$_3$-sol. (2×1 l), 1 N HCl-sol. (2×1 l) and water (2×1 l). Drying on MgSO$_4$, and concentrating under reduced pressure, yielded 25.1 g light brown crystals. These were purified by recrystallization from 2-propanol, to give 16.1 g Compound 1.2 (63%) as white crystals.
Formula: $C_{20}H_{24}O_9$
Molecular weight: 408.40
$R_f$: 0.42 (cyclohexane/ethyl acetate 1:1)
  Melting point: 149–150° C.
  IR (KBr): 2956, 1753, 1433, 1368, 1224, 1104, 1036, 978, 916, 764, 738, 702, 603 cm$^{-1}$
  ES-MS: 431=[408+Na]$^+$
  $^1$H-NMR (500 MHz, CDCl$_3$): δ 7.39 (5H, m), 5.24 (1H, dd, app. t, J=9.4 Hz), 5.24 (1H, dd, app. t, J=9.8 Hz), 5.14 (1H, dd, app. t, J=9.8 Hz), 4.40 (1H, d, J=9.9 Hz), 4.30 (1H, dd, J=17.2, 4.7 Hz), 4.16 (1H, dd, J=12.2, 1.5 Hz), 3.85 (1H, m), 2.09 (3H , s), 2.06 (3H, s), 2.01 (3H, s), 1.80 (3H, s)
  $^{13}$C-NMR (125 MHz, CDCl$_3$): δ 170.60, 170.25, 169.36, 168.70, 136.01, 128.75, 128.28, 126.96, 80.08, 75.94, 74.06, 72.44, 68.39, 62.17, 20.61, 20.48, 20.21

Synthesis of Compound 1.3

To a solution of the tetra-acetate, Compound 1.2, (16.08 g, 39.4 mmol) in a mixture of tetrahydrofuran (232 ml) and methanol (232 ml) was added anhydric potassium carbonate (1.36 g, 9.84 mmol, 0.25 eq). The mixture was stirred at room temperature under argon-atmosphere for 3 hours. Silicagel (40 ml) was added and the solvent was removed under reduced pressure. Purification of the product Compound 1.3 by column chromatography (dichloromethane/methanol 85/15) gives 9.50 g of product Compound 1.3 (99%).
Formula: $C_{12}H_{16}O_5$
Molecular weight: 240.26
$R_f$: 0.12 (dichloromethane/methanol 9:1)
  IR (KBr): 3368, 2919, 2360, 1636, 1496, 1455, 1082, 1042, 891, 764, 701, 595 cm$^{-1}$
  ES-MS: 258=[240+NH$_4$]$^+$, 263=[240+Na]$^+$
  $^1$H-NMR (500 MHz, CDCl$_3$): δ 7.44 (2H, d, J=7.1 Hz), 7.35 (2H, dd, app. t, J=7.6 Hz), 7.30 (1H, m), 4.15 (1H, d, J=9.4 Hz), 3.90 (1H, dd, J=12.1, 1.6 Hz), 3.72 (1H, dd, J=12.0, 5.2 Hz), 3.51 (1H, dd, app. t, J=8.7 Hz), 3.45 (1H, dd, app. t, J=9.4 Hz), 3.43 (3H, m), 3.40 (1H, dd, app. t, J=9.2 Hz)
  $^{13}$C-NMR (125 MHz, CDCl$_3$): δ 139.30, 127.43, 82.41, 80.70, 78.23, 74.98, 70.40, 61.41

Synthesis of Compound 1.4

To a solution of tetrol, Compound 1.3 (1.15 g, 4.79 mmol) in dry acetonitrile (3 ml) under argon-atmosphere was added camphorsulfonic acid (279 mg, 1.20 mmol, 0.25 eq) and benzaldehyde dimethyl acetal (1.44 ml, 9.58 mmol, 2 eq). The reaction mixture was stirred at room temperature for 3 hours. Subsequently the mixture was neutralized by addition of triethylamine (0.337 ml, 2.40 mmol). Concentrating the reaction mixture under reduced pressure yields 2.70 g of a light yellow oil. Purification by column chromatography (CH$_2$Cl$_2$/iPrOH 1/1) gives 1.53 g of Compound 1.4 (97%) as a white solid.
Formula: $C_{19}H_{20}O_5$
Molecular weight: 328.36
$R_f$: 0.27 (cyclohexane/ethyl acetate 1:1)
  Melting point: 114–115° C.
  $[α]_D^{20}$=+9.3°; $[α]_{365}^{20}$=+10.0° (c=1.13 in chloroform)
  IR (KBr): 3433, 2874, 2357, 1651, 1496, 1455, 1385, 1313, 1272, 1211, 1109, 1029, 1009, 913, 765, 733, 700 cm$^{-1}$
  ES-MS: 346=[328+NH$_4$]$^+$
  $^1$H-NMR (500 MHz, CDCl$_3$): δ 7.53 (2H, m), 7.40 (5H, m), 7.39 (3H, m), 5.59 (1H, s), 4.37 (1H, dd, J=10.3, 5.9 Hz), 4.30 (1H, d, J=9.3 Hz), 3.91 (1H, dd, app. t, J=8.6 Hz) 3.79 (1H, dd, app. t, J=10.3 Hz), 3.67 (1H, dd, app. t, J=9.3 Hz), 3.65 (1H, m), 3.63 (1H, m)
  $^{13}$C-NMR (125 MHz, CDCl$_3$): δ 137.50, 136.84, 129.14, 128.65, 128.52, 128.20, 127.29, 126.12, 101.73, 82.41, 80.90, 75.43, 74.60, 70.60, 68.70
  C,H-analysis: theoretical: C, 69.50%; H, 6.14%; found: C, 70.79%; H, 6.11%.

Synthesis of Compound A1

To a solution of the diol, Compound 1.4 (2.5 g, 7.6 mmol) in dry dimethyl ethylene glycol (80 ml), cooled to 0° C., was added sodium hydride (913 mg, 22.850 mmol). The reaction mixture was stirred at 0° C. under argon atmosphere for 30 minutes. Subsequently methyl iodide (1.6 ml, 25.12 mmol) was added. The reaction mixture was stirred at room temperature under argon-atmosphere for 2 hours. The reaction mixture was poured out into water (170 ml), followed by separation of layers, and extraction of the aqueous layer with diethyl ether (3×350 ml). The combined organic layers were dried over magnesium sulfate and the solvent was removed under reduced pressure to yield 3.0 g (99%) of Compound A1 as a yellow solid.
Formula: $C_{21}H_{24}O_5$
Molecular weight: 356.42
$R_f$: 0.59 (cyclohexane/ethyl acetate 8:2)
  Melting point: 97–98° C.
  $[α]_D^{20}$=−21.0°; $[α]_{365}^{20}$=67.0° (c=0.80 in chloroform)
  IR (KBr): 3035, 2925, 2851, 2360, 1497, 1455, 1378, 1276, 1173, 1104, 1030, 999, 959, 916, 765, 699 cm$^{-1}$
  ES-MS: 357=[356+H]$^+$
  $^1$H-NMR (500 MHz, CDCl$_3$): δ 7.53 (2H, m), 7.40 (3H, m), 7.38 (5H, m), 5.60 (1H, s), 4.37 (1H, dd, J=10.4, 4.9 Hz), 4.26 (1H, d, J=9.5 Hz), 3.78 (1H, dd, app. t, J=10.2 Hz), 3.69 (1H, dd, J=9.4, 9.2 Hz), 3.68 (3H, s), 3.58 (1H, ddd, J=9.9, 9.9, 4.9 Hz), 3.55 (1H, dd, J=9.1, 9.0 Hz), 3.20 (1H, dd, app. t, J=9.5, 8.5 Hz), 3.07 (3H, s)
  $^{13}$C-NMR (125 MHz, CDCl$_3$): δ 138.51, 137.19, 128.77, 128.23, 128.06, 127.25, 125.88, 100.99, 85.28, 84.25, 82.17, 81.86, 70.16, 68.78, 60.84, 60.58
  C,H-analysis: theoretical: C, 70.77%; H, 6.79%; found: C, 73.68%; H, 8.40%.

2. Synthesis of Compound A2

Figure 4:
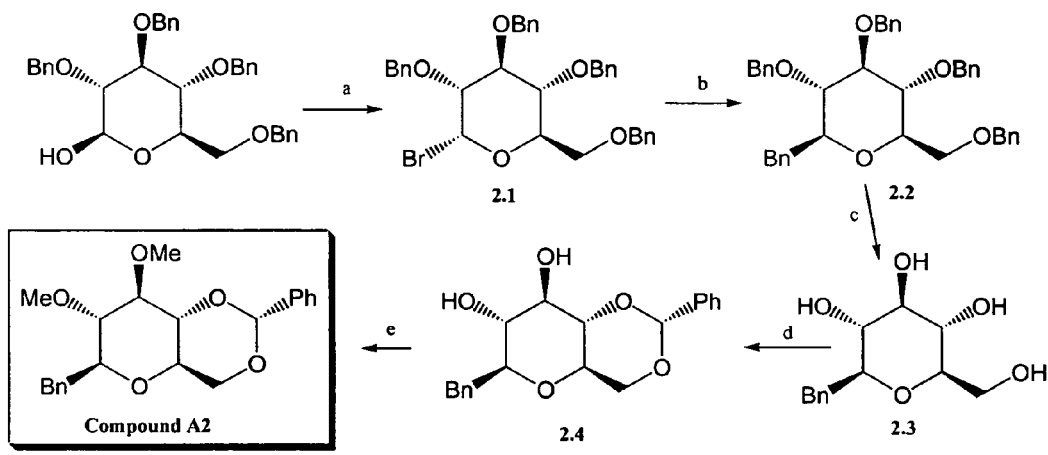
FIG. 4 is a diagrammatic representation of the scheme of synthesis of Compound A2.

The scheme of the synthesis of Compound A2 is illustrated in FIG. 4

Synthesis of Compound 2.1

To a solution of 2,3,4,6-tetra-O-benzyl-D-glucopyranose 7.35 (4.0 g, 7.4 mmol) in dry methylene chloride (50 ml) and dimethylformamide (2.5 ml) was added at room temperature a solution of oxalyl bromide (1 ml, 10 mmol) in dry methylene chloride (1 ml). The mixture was stirred at room temperature for 1 hour and then poured into ice water (50 ml). The two layers were separated and the organic layer was washed with cold water (2×50 ml), dried (MgSO$_4$) and filtered. The solvent was removed under reduced pressure to an orange-colored oil. The crude product Compound 2.1 was used in the next step.
Formula: $C_{34}H_{35}BrO_5$
Molecular weight: 603.55
$R_f$: 0.53 (cyclohexane/ethyl acetate 85:15)
$^1$H-NMR (500 MHz, CDCl$_3$): δ 7.37 (3H, m), 7.33 (5H, m), 7.31 (5H, m), 7.28 (5H, m), 7.15 (2H, m), 6.43 (1H, d, J=3.7 Hz), 4.98 (1H, d, J=5.0 Hz), 4.83 (2H, dd, app. t, J=10.9 Hz), 4.58 (1H, d, J=12.1 Hz), 4.50 (1H, d, J=10.7 Hz), 4.46 (2H, d, J=4.06 (1H, m), 4.03 (1H, dd, app. t, J=9.2 Hz), 3.80 (1H, m), 3.78 (1H, m), 3.76 (1H, d, J=4.6 Hz), 3.65 (1H, dd, J=11.0, 2.0 Hz), 3.54 (1H, dd, J=9.2, 3.7 Hz)

Synthesis of compound 2.2

To a solution of the bromide, Compound 2.1 (4.47 g, 7.4 mmol) in dry diethyl ether (100 ml) was added at 0° C. benzyl magnesium bromide (60 ml of a 1M solution in diethyl ether, 60 mmol). The mixture was stirred at 0° C. for 1 hour and at room temperature for 18 hours. Then the reaction mixture was poured into water (200 ml) and acetic acid (10 ml) was added. The two layers were separated and the organic layer was washed with a saturated sodium bicarbonate solution (3×250 ml) and brine (2×250 ml). The organic layer was dried (MgSO$_4$), filtered and the solvent was removed under reduced pressure. The crude product was purified by flash chromatography (gradient elution: cyclohexane/ethyl acetate 95/5 to 85/15), followed by HPLC (eluent:cyclohexane/diethyl ether 9/1) to yield 2.2 g (48%) of a colorless oil Compound 2.2.
Formula: $C_{41}H_{42}O_5$
Molecular weight: 614.78
$R_f$: 0.15 (cyclohexane/diethyl ether 9:1)
$[\alpha]_D^{20}$=+85.3; $[\alpha]_{365}^{20}$=+88.1(c=0.60 in chloroform)
IR (KBr): 2862, 2360, 1604, 1496, 1454, 1360, 1209, 1085, 1028, 735, 697, 668 cm$^{-1}$
ES-MS: 632=[614+NH$_4$]$^+$
$^1$H-NMR (500 MHz, CDCl$_3$): δ 7.36 (5H, m), 7.34 (5H, m), 7.31 (5H, m), 7.29 (5H, m), 7.26 (2H, m), 7.22 (3H, m), 4.96 (1H, d, J=11.0 Hz), 4.95 (1H, d, J=11.0 Hz), 4.91 (1H, d, J=11.0 Hz), 4.84 (1H, d, J=10.8 Hz), 4.69 (1H, d, J=11.0 Hz), 4.62 (1H, d, J=10.8 Hz), 4.59 (1H, d, J=12.2 Hz), 4.52 (1H, d, J=12.2 Hz), 3.74 (1H, dd, app. t, J=9.0 Hz), 3.69 (1H, m), 3.68 (1H, m), 3.66 (1H, dd, app. t, J=9.3 Hz), 3.52 (1H, ddd, J=18.3, 9.2, 2.3 Hz), 3.37 (1H, dd, app. t, J=9.0 Hz), 3.36 (1H, m), 3.17 (1H, dd, J=14.3, 2.0 Hz), 2.75 (1H, dd, J=14.3, 8.8 Hz)
$^{13}$C-NMR (125 MHz, CDCl$_3$): δ 138.68, 138.41, 138.22, 138.04, 138.01, 129.49, 128.35, 128.31, 128.26, 128.15, 127.91, 127.77, 127.69, 127.56, 127.50, 127.33, 125.95, 87.26, 81.59, 79.86, 78.80, 78.47, 75.41, 74.99, 74.81, 73.22, 68.77, 37.72
C,H-analysis: calculated: C, 80.10%; H, 6.90%; found: C, 79.38%; H, 7.09%.

Synthesis of compound 2.3

To a solution of Compound 2.2 (2.0 g, 3.25 mmol) in ethanol (80 ml) was added at room temperature palladium on carbon (Pd—C, 200 mg). The mixture was shaken (Parr apparatus) at room temperature for 2 hours under a hydrogen pressure of 4 atm. The suspension was filtered over celite, the filter was washed with ethanol and tetrahydrofuran, and the solvent was removed under reduced pressure. The crude product was purified by flash chromatography (eluent:methylene chloride/methanol 9/1) to yield 1.15 g (99%) of product Compound 2.3.

Formula: $C_{13}H_{18}O_5$
Molecular weight: 254.28
$R_f$: 0.14 (dichloromethane/methanol 9:1)
IR (KBr): 3381, 2922, 2360, 2341, 1641, 1603, 1496, 1454, 1379, 1308, 1226, 1079, 1031, 897, 754, 701, 668 cm$^{-1}$
ES-MS: 272=[254+NH$_4$]$^+$
$^1$H-NMR (500 MHz, CDCl$_3$): δ 7.29 (2H, d, J=7.0 Hz), 7.22 (2H, dd, app. t, J=7.3 Hz), 7.14 (1H, m), 3.75 (1H, dd, J=11.9, 2.4 Hz), 3.60 (1H, dd, J=11.8, 5.4 Hz), 3.35 (1H, m), 3.32 (1H, m), 3.25 (1H, dd, app. t, J=9.4 Hz), 3.15 (1H, m), 3.12 (1H, m), 3.09 (1H, dd, app. t, J=9.3 Hz), 2.69 (1H, dd, J=14.5, 8.5 Hz)
$^{13}$C-NMR (125 MHz, CDCl$_3$): δ 140.50, 130.71, 128.96, 126.97, 81.73, 81.40, 79.91, 74.91, 71.90, 62.98, 38.73
C,H-analysis: calculated: C, 61.40%; H, 7.10%; found: C, 58.92%; H, 7.15%.

Synthesis of Compound 2.4

To a solution of tetrol, Compound 2.3, (1.0 g, 3.93 mmol) in dimethylformamide (40 ml) were added at room temperature camphorsulfonic acid (274 mg, 1.18 mmol) en benzaldehyde dimethyl acetal (0.652 ml, 4.72 mmol). The mixture was stirred at 110° C. for 6 hours. It was then diluted with ethyl acetate (100 ml), washed with a 1M sodium hydroxide solution (2×150 ml), a saturated sodium bicarbonate solution (2×150 ml) and brine (2×150 ml). The organic layer was dried (MgSO$_4$), filtered and the solvent was removed under reduced pressure. The crude product was purified by flash chromatography (gradient elution:cyclohexane/ethyl acetate 9/1 to 6/4) to yield 950 mg (71%) of a white solid, Compound 2.4.
Formula: $C_{20}H_{22}O_5$
Molecular weight: 342.39
$R_f$: 0.20 (cyclohexane/ethyl acetate 6:4)
Melting point: 43–44° C.
$[\alpha]_D^{20}$=−6.9; $[\alpha]_{365}^{20}$=−10.7 (c=0.60 in chloroform)
IR (KBr): 3478, 3031, 2871, 2360, 1604, 1497, 1454, 1385, 1317, 1299, 1271, 1212, 1124, 1099, 1077, 998, 973, 919, 673, 699, 668, 655, 625, 552, 510 cm$^{-1}$
ES-MS: 343=[342+H]$^+$
$^1$H-NMR (500 MHz, CDCl$_3$): δ 7.49 (2H, m), 7.38 (3H, m), 7.31 (2H, m), 7.28 (2H, m), 7.25 (1H, m), 5.51 (1H, s), 4.28 (1H, dd, J=10.5, 4.8 Hz), 3.74 (1H, dd, app. t, J=8.7 Hz), 3.68 (1H, dd, app. t, J=10.0 Hz), 3.58 (1H, ddd, J=9.6, 8.2, 2.6 Hz), 3.43 (1H, dd, app. t, J=9.2 Hz), 3.39 (1H, m), 3.38 (1H, dd, J=10.5, 4.0 Hz), 3.18 (1H, dd, J=14.4, 2.5 Hz), 2.93 (1H, bs), 2.79 (1H, dd, J=14.4, 7.9 Hz), 2.69 (1H, bs)
$^{13}$C-NMR (125 MHz, CDCl$_3$): δ 137.84, 136.93, 129.63, 129.20, 128.26, 128.02, 126.20, 126.15, 101.69, 80.90, 80.14, 75.24, 73.58, 69.94, 68.71, 37.71
C,H-analysis: calculated: C, 70.20%; H, 6.50%; found: C, 68.84%; H, 6.59%.

Synthesis of Compound A2

To a solution of diol Compound 2.4 (920 mg, 2.69 mmol) in dry dimethyl ethylene glycol (30 ml) was added at 0° C. sodium hydride (650 mg, 16.12 mmol). The mixture was stirred at 0° C. for 30 minutes. Iodomethane (0.67 ml, 10.75 mmol) was added at 0° C. and the reaction mixture was stirred at room temperature for 16 hours. It was then poured into water (50 ml) and the two layers were separated. The water layer was extracted with ethyl acetate (3×50 ml). The combined organic layers were dried (MgSO$_4$), filtered and the solvent was removed under reduced pressure. The crude product was purified by flash chromatography (gradient elution: cyclohexane/ethyl acetate 95/5 to 7/3) to yield 907 mg (91%) of a white solid, Compound A2.

Formula: $C_{22}H_{26}O_5$
Molecular weight: 370.44
$R_f$: 0.63 (cyclohexane/ethyl acetate 6:4)
Melting point: 103–104° C.
IR (KBr): 3027, 2982, 2891, 2831, 1603, 1496, 1455, 1380, 1323, 1277, 1232, 1167, 1141, 1121, 1094, 1030, 989, 958, 875, 754, 698, 654, 622, 580, 543, 502 cm$^{-1}$
ES-MS: 371=[370+H]$^+$
$^1$H-NMR (500 MHz, CDCl$_3$): δ 7.49 (2H, m), 7.35 (3H, m), 7.29 (2H, m), 7.25 (3H, m), 5.53 (1H, s), 4.25 (1H, dd, J=10.5, 5.0 Hz), 3.67 (1H, dd, J=10.3, 5.0 Hz), 3.66 (3H, s), 3.63 (3H, s), 3.51 (1H, m), 3.49 (1H, dd, app. t, J=8.8 Hz), 3.47 (1H, m), 3.30 (1H, ddd, J=14.4, 9.5, 5.0 Hz), 3.14 (1H, dd, J=14.4, 2.1 Hz), 2.98 (1H, dd, app. t, J=8.8 Hz), 2.73 (1H, dd, J=14.3, 8.4 Hz)
$^{13}$C-NMR (125 MHz, CDCl$_3$): δ 138.20, 137.32, 129.51, 128.74, 128.06, 127.98, 126.10, 125.89, 100.92, 84.92, 82.83, 82.10, 80.23, 69.88, 68.77, 60.77, 60.59, 37.97
C,H-analysis: calculated: C, 71.30%; H, 7.10%. found: C, 71.26%; H, 7.45%.

3. Synthesis of Compound A3

Figure 5:
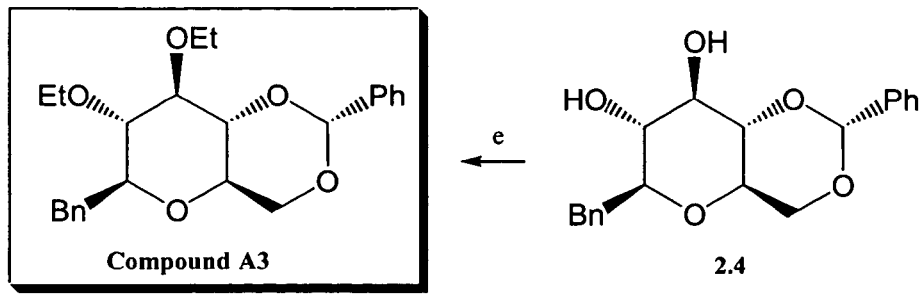
FIG. 5 is a diagrammatic representation of the scheme of synthesis of Compound A3.

The scheme of the synthesis of Compound A3 is illustrated in FIG. 5.

To a solution of diol, Compound 2.4 of the scheme of FIG. 4, (150 mg, 0.438 mmol) in dry DMF (2.2 ml) was added at 0° C. sodium_hydride (42 mg, 1.752 mmol). The mixture was stirred at 0° C. for 15 minutes. Ethyl bromide (75 μl, 1.007 mmol) was added at 0° C. and the reaction mixture was stirred at room temperature overnight. The reaction was quenched by adding MeOH. The mixture was concentrated under reduced pressure. Ether (30 ml) and water (30 ml) were added, followed by separation of layers. Extraction of the aqueous layers with ether (3×25 ml), washing the combined organic layers with brine (50 ml), drying on MgSO$_4$ and concentrating under reduced pressure yielded 180 mg solid residue. This was purified by column chromatography (230–400 mesh silica, cyclohexane:ethyl acetate 96:4), to give 130 mg of Compound A3. (75%)
Formula: $C_{24}H_{30}O_5$
Molecular weight: 398.49
$R_f$: 0.20 (cyclohexane/ethyl acetate 95:5)
Melting point: 87–89° C.
IR (KBr): 2973 (m), 2868 (m), 1496 (m), 1454 (m), 1374 (m), 1276 (m), 1170 (m), 1142 (m), 1087 (s), 1029 (m), 1008 (m), 698 (m)
ES-MS: 399=[M+H]$^+$
$^1$H-NMR (500 MHz, CDCl$_3$): δ 7.48 (2H, m), 7.36 (3H, m), 7.25 (5H, m), 5.52 (1H, s), 4.24 (1H, dd, J=10.4, 5.0 Hz), 3.98 (2H, m), 3.75 (1H, m), 3.67 (2H, m), 3.54 (2H, m), 3.49 (1H, dd, app. t, J=9.1 Hz), 3.29 (1H, ddd, app. dt, J=9.9, 5.0 Hz), 3.15 (1H, dd, J=14.3, 2.1 Hz), 3.09 (1H, dd, app. t, J=9.1 Hz), 2.72 (1H, dd, J=14.3, 8.6 Hz), 1.24 (3H, t, J=7.1 Hz), 1.22 (3H, t, J=7.0 Hz)
APT-NMR (125 MHz, CDCl$_3$): δ 138.6 (C), 137.6 (C), 129.7 (CH), 128.9 (CH), 128.3 (CH), 128.2 (CH), 126.3 (CH), 126.1 (CH), 101.1 (CH), 83.4 (CH), 82.2 (CH), 81.8 (CH), 80.7 (CH), 70.3 (CH), 69.0 (CH$_2$), 68.9 (CH$_2$), 68.6 (CH$_2$), 38.3 (CH$_2$), 16.0 (CH$_3$), 15.9 (CH$_3$)

4. Synthesis of Compound A4

Figure 6:
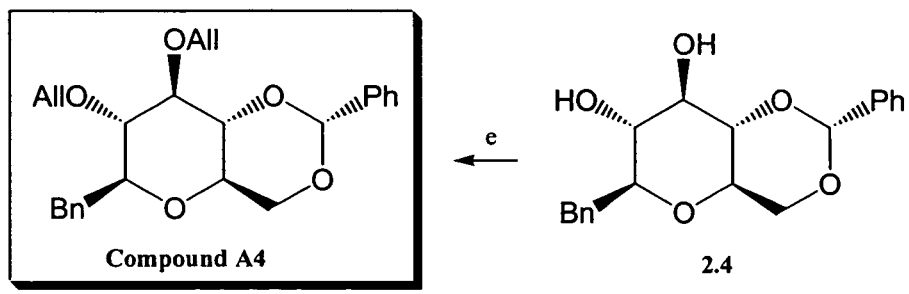
FIG. 6 is a diagrammatic representation of the scheme of synthesis of Compound A4.

The scheme of the synthesis of Compound A4 is illustrated in FIG. 6.

To a solution of diol, Compound 2.4 of the scheme of FIG. 4, (250 mg, 0.730 mmol) in dry DMF (3.5 ml) was added at 0° C. sodium hydride (70 mg, 2.92 mmol). The mixture was stirred at 0° C. for 20 minutes. Allyl bromide (145 μl, 1.679 mmol) was added at 0° C. and the reaction mixture was stirred at room temperature overnight. The reaction was quenched by adding MeOH. Ether (30 ml) and water (30 ml) were added, followed by separation of layers. Extraction of the aqueous layers with ether (3×30 ml), washing the combined organic layers with brine (50 ml), drying on MgSO$_4$ and concentrating under reduced pressure yielded 314 mg solid residue. This was purified by column chromatography (230–400 mesh silica, cyclohexane:ethyl acetate 96:4), to give 231 mg of Compound A4. (76%)
Formula: $C_{26}H_{30}O_5$
Molecular weight: 422.51
$R_f$: 0.69 (cyclohexane/ethyl acetate 1:1)
Melting point: 58–60° C.
IR (KBr): cm$^{-1}$ 2867 (m), 1454 (m), 1383 (m), 1171 (m), 1101 (s), 1084 (s), 1033 (m), 1000 (m), 972 (m), 921 (m), 747 (m), 691 (s)
ES-MS: 423=[M+H]$^+$
$^1$H-NMR (500 MHz, CDCl$_3$): δ (ppm) 7.47 (2H, dd, J=7.7, 1.7 Hz), 7.38–7.34 (3H, m), 7.30–7.20 (5H, m), 6.00–5.91 (2H, m), 5.52 (1H, s), 5.32 (1H, dd, J=17.2, 1.6 Hz), 5.28 (1H, dd, J=17.2, 1.7 Hz), 5.20 (1H, dd, J=10.4, 1.6 Hz), 5.16 (1H, dd, J=10.4, 1.7 Hz), 4.47 (1H, dd, J=12.3, 5.6 Hz), 4.43 (1H, dd, J=12.6, 5.6 Hz), 4.26–4.21 (2H, m), 4.15 (1H, dd, J=12.3, 5.8 Hz), 3.66 (1H, dd, app. t, J=10.3 Hz), 3.65 (1H, dd, app. t, J=9.0 Hz), 3.57 (1H, ddd, app. dt, J=9.4, 2.3 Hz), 3.54 (1H, dd, app. t, J=9.3 Hz), 3.31 (1H, ddd, app. dt, J=9.9, 5.0 Hz), 3.17 (2H, m), 2.72 (1H, dd, J=14.4, 8.5 Hz)
APT-NMR (125 MHz, CDCl$_3$): δ (ppm) 138.4 (C), 137.5 (C), 135.2 (CH), 134.9 (CH), 129.7 (CH), 128.9 (CH), 128.3 (CH), 128.2 (CH), 126.3 (CH), 126.1 (CH), 117.1 (CH$_2$), 116.9 (CH$_2$), 101.1 (CH), 83.1 (CH), 82.3 (CH), 81.2 (CH), 80.5 (CH), 74.4 (CH$_2$), 73.9 (CH$_2$), 70.2 (CH), 69.0 (CH$_2$), 38.2 (CH$_2$)

5. Synthesis of Compound A5

Figure 7:
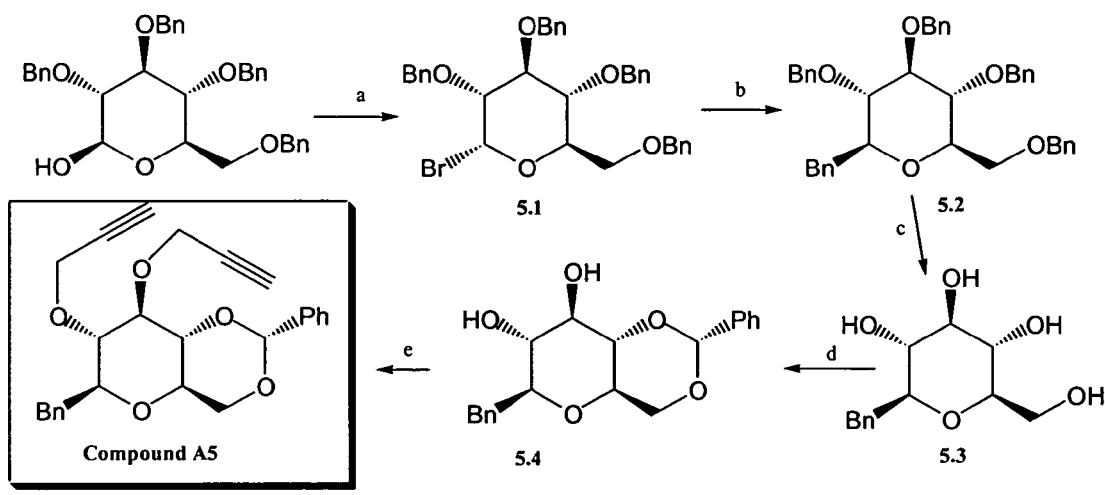
FIG. 7 is a diagrammatic representation of the scheme of synthesis of Compound A5.

The scheme of the synthesis of Compound A5 is illustrated in FIG. 7.

Synthesis of Compound 5.1

To a solution of 2,3,4,6-tetra-O-benzyl-D-glucopyranose (4.0 g, 7.4 mmol) in dry methylene chloride (50 ml) and dimethylformamide (2.5 ml) was added at room temperature a solution of oxalyl bromide (1 ml, 10 mmol) in dry methylene chloride (1 ml). The mixture was stirred at room temperature for 1 hour and then poured into ice-water (50 ml). The two layers were separated and the organic layer was washed with cold water (2×50 ml), dried (MgSO$_4$) and filtered. The solvent was removed under reduced pressure to an orange colored oil. The crude product Compound 5.1 was used in the next step.
Formula: $C_{34}H_{35}BrO_5$
Molecular weight: 603.55
$R_f$: 0.53 (cyclohexane/ethyl acetate 85:15)
$^1$H-NMR (500 MHz, CDCl$_3$): δ 7.37 (3H, m), 7.33 (5H, m), 7.31 (5H, m), 7.28 (5H, m), 7.15 (2H, m), 6.43 (1H, d, J=3.7 Hz), 4.98 (1H, d, J=5.0 Hz), 4.83 (2H, dd, app. t, J=10.9 Hz), 4.58 (1H, d, J=12.1 Hz), 4.50 (1H, d, J=10.7 Hz), 4.46 (2H, d, J=12.1 Hz), 4.06 (1H, m), 4.03 (1H, dd, app. t, J=9.2 Hz), 3.80 (1H, m), 3.78 (1H, m), 3.76 (1H, d, J=4.6 Hz), 3.65 (1H, dd, J=11.0, 2.0 Hz), 3.54 (1H, dd, J=9.2, 3.7 Hz)

Synthesis of Compound 5.2

To a solution of bromide 5.1 (4.47 g, 7.4 mmol) in dry diethyl ether (100 ml) was added at 0° C. benzylmagnesium bromide (60 ml of a 1M solution in diethyl ether, 60 mmol). The mixture was stirred at 0° C. for 1 hour and at room temperature for 18 hours. Then the reaction mixture was poured into water (200 ml) and acetic acid (10 ml) was added. The two layers were separated and the organic layer was washed with a saturated sodium bicarbonate solution (3×250 ml) and brine (2×250 ml). The organic layer was dried (MgSO$_4$), filtered and the solvent was removed under reduced pressure. The crude product was purified by flash chromatography (gradient elution: cyclohexane/ethyl acetate 95/5 to 85/15), followed by HPLC (eluens: cyclohexane/diethyl ether 9/1) to yield 2.2 g (48%) of a colorless oil Compound 5.2.

Formula: $C_{41}H_{42}O_5$

Molecular weight: 614.78

$R_f$: 0.15 (cyclohexane/diethyl ether 9:1)

$[\alpha]_D^{20}$=+85.3; $[\alpha]_{365}^{20}$=+88.1 (c=0.60 in chloroform)

IR (KBr): 2862, 2360, 1604, 1496, 1454, 1360, 1209, 1085, 1028, 735, 697, 668 cm$^{-1}$

ES-MS: 632=[614+NH$_4$]$^+$ $^1$H-NMR (500 MHz, CDCl$_3$): δ 7.36 (5H, m), 7.34 (5H, m), 7.31 (5H, m), 7.29 (5H, m), 7.26 (2H, m), 7.22 (3H, m), 4.96 (1H, d, J=11.0 Hz), 4.95 (1H, d, J=11.0 Hz), 4.91 (1H, d, J=11.0 Hz), 4.84 (1H, d, J=10.8 Hz), 4.69 (1H, d, J=11.0 Hz), 4.62 (1H, d, J=10.8 Hz), 4.59 (1H, d, J=12.2 Hz), 4.52 (1H, d, J=12.2 Hz), 3.74 (1H, dd, app. t, J=9.0 Hz), 3.69 (1H, m), 3.68 (1H, m), 3.66 (1H, dd, app. t, J=9.3 Hz), 3.52 (1H, ddd, J=18.3, 9.2, 2.3 Hz), 3.37 (1H, dd, app. t, J=9.0 Hz), 3.36 (1H, m), 3.17 (1H, dd, J=14.3, 2.0 Hz), 2.75 (1H, dd, J=14.3, 8.8 Hz)

$^{13}$C-NMR (125 MHz, CDCl$_3$): δ 138.68, 138.41, 138.22, 138.04, 138.01, 129.49, 128.35, 128.31, 128.26, 128.15, 127.91, 127.77, 127.69, 127.56, 127.50, 127.33, 125.95, 87.26, 81.59, 79.86, 78.80, 78.47, 75.41, 74.99, 74.81, 73.22, 68.77, 37.72

C,H-analysis: calculated: C, 80.10%; H, 6.90%. found: C, 79.38%; H, 7.09%.

Synthesis of Compound 5.3

To a solution of Compound 5.2 (2.0 g, 3.25 mmol) in ethanol (80 ml) was added at room temperature palladium on carbon (Pd—C, 200 mg). The mixture was shaken (Parr apparatus) at room temperature for 2 hours under a hydrogen pressure of 4 atm. The suspension was filtered over celite, the filter was washed with ethanol and tetrahydrofuran, and the solvent was removed under reduced pressure. The crude product was purified by flash chromatography (eluent:methylene chloride/methanol 9/1) to yield 1.15 g (99%) of product Compound 5.3.

Formula: $C_{13}H_{18}O_5$

Molecular weight: 254.28

$R_f$: 0.14 (dichloromethane/methanol 9:1)

IR (KBr): 3381, 2922, 2360, 2341, 1641, 1603, 1496, 1454, 1379, 1308, 1226, 1079, 1031, 897, 754, 701, 668 cm$^{-1}$

ES-MS: 272=[254+NH$_4$]$^+$ $^1$H-NMR (500 MHz, CDCl$_3$): δ 7.29 (2H, d, J=7.0 Hz), 7.22 (2H, dd, app. t, J=7.3 Hz), 7.14 (1H, m), 3.75 (1H, dd, J=11.9, 2.4 Hz), 3.60 (1H, dd, J=11.8, 5.4 Hz), 3.35 (1H, m), 3.32 (1H, m), 3.25 (1H, dd, app. t, J=9.4 Hz), 3.15 (1H, m), 3.12 (1H, m), 3.09 (1H, dd, app. t, J=9.3 Hz), 2.69 (1H, dd, J=14.5, 8.5 Hz)

$^{13}$C-NMR (125 MHz, CDCl$_3$): δ 140.50, 130.71, 128.96, 126.97, 81.73, 81.40, 79.91, 74.91, 71.90, 62.98, 38.73

C,H-analysis: calculated: C, 61.40%; H, 7.10%. found: C, 58.92%; H, 7.15%.

Synthesis of Comnpound 5.4

To a solution of tetrol Compound 5.3 (1.0 g, 3.93 mmol) in dimethylformamide (40 ml) were added at room temperature camphorsulfonic acid (274 mg, 1.18 mmol) en benzaldehyde dimethyl acetal (0.652 ml, 4.72 mmol). The mixture was stirred at 110° C. for 6 hours. It was then diluted with ethyl acetate (100 ml), washed with a 1M sodium hydroxide solution (2×150 ml), a saturated sodium bicarbonate solution (2×150 ml) and brine (2×150 ml). The organic layer was dried (MgSO$_4$), filtered and the solvent was removed under reduced pressure. The crude product was purified by flash chromatography (gradient elution: cyclohexane/ethyl acetate 9/1 to 6/4) to yield 950 mg (71%) of a white solid Compound 5.4.

Formula: $C_{20}H_{22}O_5$

Molecular weight: 342.39

$R_f$: 0.20 (cyclohexane/ethyl acetate 6:4)

Melting point: 43–44° C.

$[\alpha]_D^{20}$=−6.9; $[\alpha]_{365}^{20}$=−10.7 (c=0.60 in chloroform)

IR (KBr): 3478, 3031, 2871, 2360, 1604, 1497, 1454, 1385, 1317, 1299, 1271, 1212, 1124, 1099, 1077, 998, 973, 919, 673, 699, 668, 655, 625, 552, 510 cm$^{-1}$

ES-MS: 343=[342+H]$^+$ $^1$H-NMR (500 MHz, CDCl$_3$): δ 7.49 (2H, m), 7.38 (3H, m), 7.31 (2H, m), 7.28 (2H, m), 7.25 (1H, m), 5.51 (1H, s), 4.28 (1H, dd, J=10.5, 4.8 Hz), 3.74 (1H, dd, app. t, J=8.7 Hz), 3.68 (1H, dd, app. t, J=10.0 Hz), 3.58 (1H, ddd, J=9.6, 8.2, 2.6 Hz), 3.43 (1H, dd, app. t, J=9.2 Hz), 3.39 (1H, m), 3.38 (1H, dd, J=10.5, 4.0 Hz), 3.18 (1H, dd, J=14.4, 2.5 Hz), 2.93 (1H, bs), 2.79 (1H, dd, J=14.4, 7.9 Hz), 2.69 (1H, bs)

$^{13}$C-NMR (125 MHz, CDCl$_3$): δ 137.84, 136.93, 129.63, 129.20, 128.26, 128.02, 126.20, 126.15, 101.69, 80.90, 80.14, 75.24, 73.58, 69.94, 68.71, 37.71

C,H-analysis: calculated: C, 70.20%; H, 6.50%. found: C, 68.84%; H 6.59%.

Synthesis of Compound A5

To a solution of diol Compound 5.4 (80 mg, 0.234 mmol) in dry THF (410 µL) was added at 0° C. sodium hydride (23 mg of a 60% dispersion, 2.2 eq). The mixture was heated to reflux-temperature and stirred as such for 1.5 h. After cooling the reaction mixture to 0° C., tetra-n-butylammonium iodide (1.8 mg, 0.02 eq) and propargyl bromide (57 µl, 2.2 eq) were added. The reaction mixture is stirred at room temperature overnight, after which starting material is still present, so extra portions of sodium hydride (13 mg 60% dispersion, 1.1 eq) and tetra-n-butylammonium iodide (1.8 mg, 0.02 eq) were added. Stirring was continued at room temperature during 2.5 h. Work-up was started by pouring out in water (50 ml), followed by extraction with diethyl ether (3×40 ml). The combined organic layers were washed with brine (50 ml) and dried over MgSO$_4$. Filtration and concentration in vacuo yielded 104 mg crude product, which was purified by column chromatography (230–400 mesh silica, pentane:ether 85:15). This gave 83 mg Compound A5 as a white crystalline product. (86%)

Formula: $C_{26}H_{26}O_5$

Molecular weight: 418.48

$R_f$: 0.26 (pentane:ether 85:15)

Melting point: 81–83° C.

$[\alpha]_D^{20}$=−45.0°; $[\alpha]_{365}^{20}$=−132.8° (c=1.02 in chloroform)

IR (KBr): 3288 (s), 3037 (m), 2931 (m), 2872 (s), 1454 (m), 1355 (m), 1102 (s), 1085 (s), 1032 (s), 1008 (s), 973 (m), 750 (m), 697 (s), 656 (m), 636 (m)

ES-MS: 419=[M+H]$^+$

EI-MS: (m/z) 69 (23), 91 (100), 105 (58), 149 (17), 171 (10), 221 (2), 247 (2), 269 (2), 327 (3), 379 (11) [M$^+$–39]

$^1$H-NMR (500 MHz, CDCl$_3$): δ 7.47–7.45 (2H, m), 7.39–7.35 (3H, m), 7.31–7.21 (5H, m), 5.51 (1H, s), 4.62 (1H, dd, J=15.7, 2.4 Hz), 4.52 (1H, dd, J=15.7, 2.4 Hz), 4.50 (1H, dd, J=15.7, 2.4 Hz), 4.43 (1H, dd, J=15.7, 2.4 Hz), 4.25 (1H, dd, J=10.5, 5.0 Hz), 3.83 (1H, dd, J=9.1, 8.6 Hz), 3.67 (1H, dd, app. t, J=10.3 Hz), 3.58 (1H, dd, app. t, J=9.4 Hz), 3.55 (1H, ddd, app. dt, J=9.0, 2.2 Hz), 3.36–3.27 (3H, m), 2.73 (1H, dd, J=14.5, 8.7 Hz), 2.50 (1H, t, J=2.4 Hz), 2.48 (1H, t, J=2.4 Hz)

APT-NMR (125 MHz, CDCl$_3$): δ 138.4 (C), 137.2 (C), 129.7 (CH), 129.0 (CH), 128.3 (CH), 128.1 (CH), 126.3 (CH), 126.0 (CH), 101.1 (CH), 82.6 (CH), 82.2 (CH), 80.1 (CH), 79.5 (CH), 74.7 (C), 74.5 (C), 69.8 (CH), 68.8 (CH$_2$), 60.2 (CH$_2$), 59.7 (CH$_2$), 38.1 (CH$_3$)

6. Synthesis of compound A6.

Figure 8:
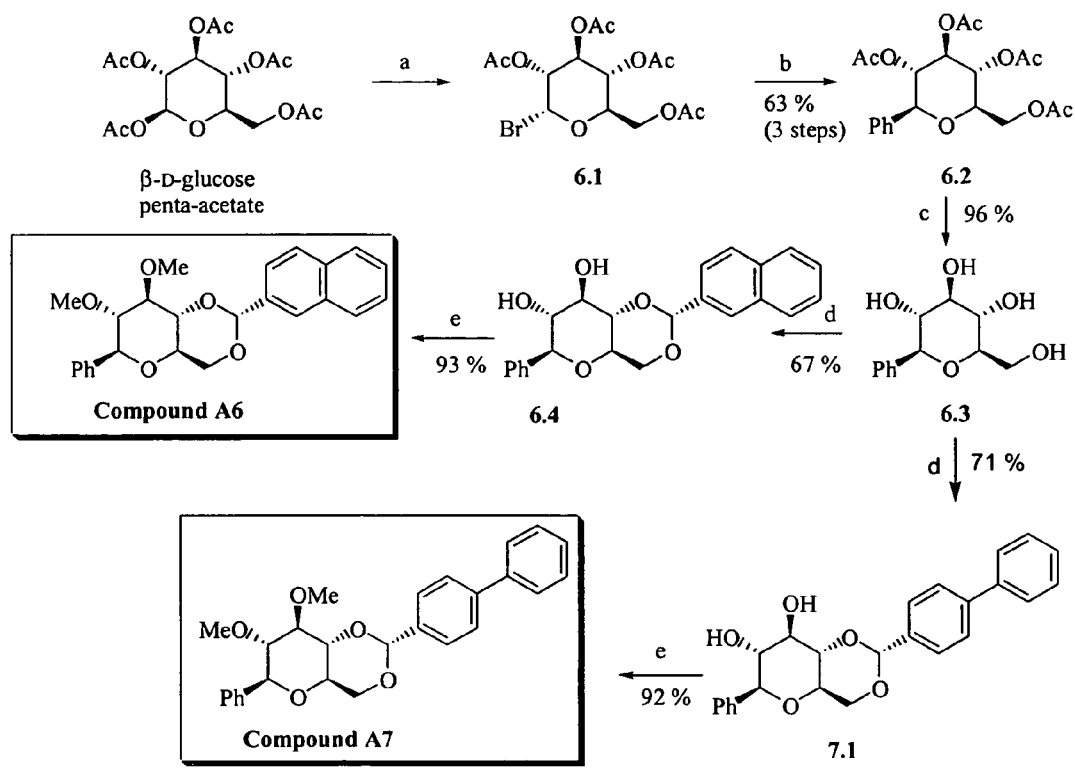
FIG. 8 is a diagrammatic representation of the scheme of synthesis of Compounds A6 and A7.

The scheme of the synthesis of Compound A6 is illustrated in FIG. 8.

Synthesis of Compound 6.1

To (β)-D-glucose penta-acetate (24.6 g, 63.0 mmol) was added a solution of hydrogen bromide in acetic acid (33 wt %, 100 ml). A dark-brown color immediately appears. The reaction mixture was stirred at room temperature for 30 minutes under argon atmosphere. Subsequently the solvent was removed by azeotropic distillation in vacuo with toluene (4×50 ml), yielding a green-brown solid Compound 6.1. The crude product was used in the next reaction step without further purification.

Formula: C$_{14}$H$_{19}$O$_9$Br

Molecular weight: 411.20

R$_f$: 0.46 (cyclohexane/ethyl acetate 1:1)

IR (KBr): 2962, 2360, 2342, 1748, 1435, 1369, 1218, 1162, 1112, 1079, 1042, 911, 752, 668, 601, 563 cm$^{-1}$

ES-MS: 433=[410+Na]$^+$, 435=[412+Na$^+$]

$^1$H-NMR (500 MHz, CDCl$_3$): δ 6.61 (1H, d, J=4.0 Hz), 5.56 (1H, dd, app. t, J=9.7 Hz), 5.16 (1H, dd, app. t, J=9.7 Hz), 4.84 (1H, dd, J=10.0, 4.0 Hz), 4.33 (1H, m), 4.30 (1H, m), 4.13 (1H, dd, J=12.3, 1.5 Hz), 2.11 (3H, s), 2.10 (3H, s), 2.05 (3H, s), 2.03 (3H, s)

$^{13}$C-NMR (125 MHz, CDCl$_3$): δ 170.37, 169.70, 169.64, 169.31, 86.34, 71.91, 70.39, 69.94, 66.94, 60.76, 20.48, 20.48, 20.38, 20.38

Synthesis of Compound 6.2

To a solution of phenylmagnesium bromide (200 ml of a 3M solution in diethyl ether, 600 mmol, 9.5 eq) in dry diethyl ether (500 ml), cooled to 0° C., was added a solution of bromide Compound 6.1 (63.0 mmol theoretical) in dry diethyl ether (500 ml) by canulation. The reaction mixture was stirred at room temperature under argon-atmosphere for 72 hours. Subsequently the reaction mixture was poured out into water (2000 ml), and acetic acid (200 ml) was added to dissolve the magnesium-salts. The two layers were separated, and the organic layer was washed with water (3×500 ml). The combined aqueous layers were concentrated under reduced pressure to yield a light-brown solid residue. This residue was dissolved in pyridine (500 ml). At 0° C. acetic anhydride (340 ml) was added slowly. After adding DMAP (200 mg, 1.64 mmol), stirring was continued for 20 hours at room temperature under argon-atmosphere. Next the reaction mixture was concentrated under reduced pressure, followed by azeotropic distillation with toluene (1×250 ml), and the addition of diethyl ether (3 l). The obtained organic layer was washed with sat. NaHCO$_3$-sol. (2×1 l), 1 N HCl-sol. (2×1 l) and water (2×1 l). Drying on MgSO$_4$, and concentrating under reduced pressure, yielded 25.1 g light-brown crystals. These were purified by recrystallization from 2-propanol, to give 16.1 g Compound 6.2 (63%) as white crystals.

Formula: C$_{20}$H$_{24}$O$_9$

Molecular weight: 408.40

R$_f$: 0.42 (cyclohexane/ethyl acetate 1:1)

Melting point: 149–150° C.

IR (KBr): 2956, 1753, 1433, 1368, 1224, 1104, 1036, 978, 916, 764, 738, 702, 603 cm$^{-1}$

ES-MS: 431=[408+Na]$^+$ $^1$H-NMR (500 MHz, CDCl$_3$): δ 7.39 (5H, m), 5.24 (1H, dd, app. t, J=9.4 Hz), 5.24 (1H, dd, app. t, J=9.8 Hz), 5.14 (1H, dd, app. t, J=9.8 Hz), 4.40 (1H, d, J=9.9 Hz), 4.30 (1H, dd, J=17.2, 4.7 Hz), 4.16 (1H, dd, J=12.2, 1.5 Hz), 3.85 (1H, m), 2.09 (3H, s), 2.06 (3H, s), 2.01 (3H, s), 1.80 (3H, s)

$^{13}$C-NMR (125 MHz, CDCl$_3$): δ 170.60, 170.25, 169.36, 168.70, 136.01, 128.75, 128.28, 126.96, 80.08, 75.94, 74.06, 72.44, 68.39, 62.17, 20.61, 20.48, 20.21

Synthesis of Compound 6.3

To a solution of tetra-acetate Compound 6.2 (16.08 g, 39.4 mmol) in a mixture of tetrahydrofuran (232 ml) and methanol (232 ml) was added anhydric potassium carbonate (1.36 g, 9.84 mmol, 0.25 eq). The mixture was stirred at room temperature under argon-atmosphere for 3 hours. Silicagel (40 ml) was added and the solvent was removed under reduced pressure. Purification of the product Compound 6.3 by column chromatography (dichloromethane/methanol 85/15) gives 9.50 g of product 6.3 (99%).

Formula: C$_{12}$H$_{16}$O$_5$

Molecular weight: 240.26

R$_f$: 0.12 (dichloromethane/methanol 9:1)

IR (KBr): 3368, 2919, 2360, 1636, 1496, 1455, 1082, 1042, 891, 764, 701, 595 cm$^{-1}$

ES-MS: 258=[240+NH$_4$]$^+$, 263=[240+Na]$^+$ $^1$H-NMR (500 MHz, CDCl$_3$): δ 7.44 (2H, d, J=7.1 Hz), 7.35 (2H, dd, app. t, J=7.6 Hz), 7.30 (1H, m), 4.15 (1H, d, J=9.4 Hz), 3.90 (1H, dd, J=12.1, 1.6 Hz), 3.72 (1H, dd, J=12.0, 5.2 Hz), 3.51 (1H, dd, app. t, J=8.7 Hz), 3.45 (1H, dd, app. t, J=9.4 Hz), 3.43 (3H, m), 3.40 (1H, dd, app. t, J=9.2 Hz)

$^{13}$C-NMR (125 MHz, CDCl$_3$): δ 139.30, 127.43, 82.41, 80.70, 78.23, 74.98, 70.40, 61.41

Synthesis of Compound 6.4

To a solution of tetrol Compound 6.3 (300 mg, 1.25 mmol) in dry acetonitrile (12 ml) under argon-atmosphere were added camphorsulfonic acid (30 mg, 0.1 eq), anhydr. cupper(II) sulfate (300 mg, 1.5 eq), and 2-naphtaldehyde (975 mg, 5 eq). The reaction mixture was heated to reflux temperature. After stirring as such for 12 h the reaction was poured out into water (50 ml), followed by extraction of the aqueous layer with dichloromethane (3×50 ml). The combined organic layers were washed with brine (50 ml), neutralized with triethylamine and dried on MgSO$_4$. Filtration and concentration in vacuo gave 370 mg residue which was purified by column chromatography (230–400 mesh silica, dichloromethane:isopropanol 98:2) and HPLC (dichloromethane:isopropanol 100:2.5, UV-detection at 280 nm). This yielded 318 mg pure Compound 6.4 as a solid (67%).

Formula: C$_{23}$H$_{22}$O$_5$

Molecular weight: 378.42

R$_f$: 0.28 (dichloromethane/isopropanol 97.5/2.5)

Melting point: 211–212°C $[α]_D^{20}$=–18.6°; $[α]_{365}^{20}$=–60.3° (c=1.00 in methanol)

IR (KBr): 3412 (m), 2872 (m), 1455 (m), 1390 (m), 1373 (m), 1344 (m), 1267 (m), 1173 (m), 1126 (s), 1107 (s), 1073 (s), 1032 (m), 1009 (s), 973 (m), 897 (m), 861 (m), 820 (m) 761 (m), 744 (m), 701 (s), 579 (m), 479 (m) cm$^{-1}$

EI-MS: (m/z) 91 (38), 128 (38), 156 (100), 378 (35) [M$^+$]

$^1$H-NMR (500 MHz, CDCl$_3$): δ 8.03 (1H, s), 7.92 (3H, m), 7.65 (1H, dd, J=8.5, 1.6 Hz), 7.52 (2H, m), 7.41 (2H, br d, J=7.0 Hz), 7.30 (3H, m), 5.80 (1H, s), 4.64 (1H, br s), 4.34 (1H, d, J=9.5 Hz), 4.28 (1H, dd, J=10.2, 4.8 Hz), 4.24 (1H, br s), 3.82 (1H, dd, app. t, J=10.2 Hz), 3.81 (1H, m), 3.68 (1H, dd, app. t, J=9.1 Hz), 3.63 (1H, ddd, J=10.0, 9.3, 4.8 Hz), 3.54 (1H, br t, J=8.9 Hz)

APT-NMR (125 MHz, CDCl$_3$): δ 140.7 (C), 136.7 (C), 134.5 (C), 133.8 (C), 129.1 (CH), 128.7 (CH), 128.6 (CH), 128.5 (CH), 128.5 (CH), 127.2 (CH), 127.0 (CH), 126.5 (CH), 125.2 (CH), 102.2 (CH), 83.6 (CH), 82.6 (CH), 76.9 (CH), 76.0 (CH), 71.7 (CH), 69.5 (CH$_2$)

Synthesis of Compound A6

To a solution of Compound 6.4 (150 mg, 0.396 mmol) in dry DMF (3.96 ml), cooled to 0° C., was added sodium hydride (65 mg of a 60% dispersion, 4 eq). The reaction mixture was stirred at 0° C. under argon atmosphere for 30 minutes. Subsequently methyl iodide (125 μl, 5 eq) was added. The reaction mixture was stirred at room temperature under argon-atmosphere for 15 hours. The reaction mixture was poured out into water (50 ml), followed by separation of layers, and extraction of the aqueous layer with diethyl ether (3×50 ml). The combined organic layers were washed with brine (50 ml), dried over magnesium sulfate and the solvent was removed under reduced pressure. The residue was purified by column chromatography (230–400 mesh silica, pentane:dichloromethane:ether 10:10:0.25), to yield 149 mg Compound A6 as a white solid. (93%).

Formula: C$_{25}$H$_{26}$O$_5$

Molecular weight: 406.47

R$_f$: 0.24 (pentane:dichloromethane:ether 10:10:0.25)

Melting point: 135° C.

$[α]_D^{20}$=-27.6°; $[α]_{365}^{20}$=-103.7° (c=1.03 in chloroform)

IR (KBr): 2932 (m), 2896 (m), 2834 (m), 1174 (m), 1142 (m), 1104 (s), 1088 (m), 1044 (m), 1033 (m), 1003 (m), 959 (m), 858 (m), 822 (m), 764 (m), 700 (m) cm$^{-1}$

EI-MS: (m/z) 45 (19), 88 (45), 121 (100), 156 (53), 199 (22), 406 (9) [M$^+$]

$^1$H-NMR (500 MHz, CDCl$_3$): δ 8.00 (1H, s), 7.88–7.84 (3H, m), 7.63 (1H, dd, J=8.5, 1.6 Hz), 7.50–7.48 (2H, m), 7.42–7.32 (5H, m), 5.76 (1H, s), 4.42 (1H, dd, J=10.4, 5.0 Hz), 4.28 (1H, d, J=9.6 Hz), 3.84 (1H, dd, app. t, J=10.2 Hz), 3.75 (1H, dd, app. t, J=9.3 Hz), 3.70 (3H, s), 3.62 (1H, ddd, app. dt, J=9.8, 5.0 Hz), 3.58 (1H, dd, app. t, J=9.3 Hz), 3.22 (1H, dd, J=9.5, 8.6 Hz), 3.08 (3H, s)

APT-NMR (125 MHz, CDCl$_3$): δ 138.8 (C), 134.9 (C), 133.7 (C), 133.0 (C), 128.5 (CH), 128.1 (CH), 127.7 (CH), 127.5 (CH), 126.4 (CH), 126.2 (CH), 125.6 (CH), 123.8 (CH), 101.5 (CH), 85.6 (CH), 84.6 (CH), 82.5 (CH), 82.3 (CH), 70.8 (CH), 69.2 (CH$_2$), 61.0 (CH$_3$), 60.8 (CH$_3$)

7. Synthesis of Compound A7

The scheme of the synthesis of Compound A7 is illustrated in FIG. 8.

Synthesis of Compound 7.1

To a solution of tetrol Compound 6.3 (300 mg, 1.25 mmol) in dry acetonitrile (12 ml) under argon-atmosphere were added camphorsulfonic acid (30 mg, 0.1 eq), anhydr. cupper(II) sulfate (300 mg, 1.5 eq), and 4-biphenylcarboxaldehyde (1.15 g, 5 eq). The reaction mixture was heated to reflux temperature. After stirring as such for 24 h the reaction was poured out into water (50 ml), followed by extraction of the aqueous layer with dichloromethane (3×50 ml). The combined organic layers were washed with brine (50 ml), neutralized with triethylamine and dried on MgSO$_4$. Filtration and concentration in vacuo gave 370 mg residue which was purified by column chromatography (230–400 mesh silica, gradient: pure dichloromethane to dichloromethane:isopropanol 98:2). This yielded 360 mg pure Compound 7.1 as a solid (71%).

Formula: C$_{25}$H$_{24}$O$_5$

Molecular weight: 404.46

R$_f$: 0.22 (dichloromethane/isopropanol 98/2)

Melting point: 195–197° C.

$[α]_D^{20}$=-0.49°; $[α]_{365}^{20}$=-8.02° (c=1.03 in chloroform)

IR (KBr): 3412 (m), 2867 (m), 1385 (m), 1108 (s), 1077 (s), 1033 (m), 1008 (s), 984 (m), 836 (m), 766 (s), 699 (s) cm$^{-1}$

EI-MS: (m/z) 60 (16), 91 (55), 120 (28), 152 (39), 182 (100), 225 (3), 327 (3), 404 (26) [M$^+$]

$^1$H-NMR (500 MHz, CDCl$_3$): δ 7.67–7.66 (4H, m), 7.61 (2H, d, J=8.2 Hz), 7.48–7.28 (8H, m), 5.70 (1H, s), 4.64 (1H, d, J=3.8 Hz), 4.34 (1H, d, J=9.5 Hz), 4.26 (1H, dd, J=10.3, 4.8 Hz), 4.24 (1H, d, J=4.8 Hz), 3.82–3.76 (2H, m), 3.65 (1H, dd, app. t, J=9.2 Hz), 3.60 (1H, ddd, app. dt, J=9.5, 4.6 Hz), 3.54 (1H, ddd, app. dt, J=9.1, 4.9 Hz)

APT-NMR (125 MHz, CDCl$_3$): δ 142.2 (C), 141.4 (C), 140.7 (C), 138.3 (C), 129.7 (CH), 128.7 (CH), 128.6 (CH), 128.5 (CH), 128.3 (CH), 127.8 (CH), 127.8 (CH), 127.3 (CH), 101.9 (CH), 83.6 (CH), 82.5 (CH), 76.9 (CH), 76.0 (CH), 71.7 (CH), 69.4 (CH$_2$)

Synthesis of compound A7

To a solution of Compound 7.1 (150 mg, 0.371 mmol) in dry DMF (5 ml), cooled to 0° C., was added sodium hydride (60 mg of a 60% dispersion, 4 eq). The reaction mixture was stirred at 0° C. under argon atmosphere for 30 minutes. Subsequently methyl iodide (120 μl, 5 eq) was added. The reaction mixture was stirred at room temperature under argon-atmosphere for 16 hours. The reaction mixture was poured out into water (50 ml), followed by separation of layers, and extraction of the aqueous layer with diethyl ether (3×50 ml). The combined organic layers were washed with brine (50 ml), dried over magnesium sulfate and the solvent was removed under reduced pressure. The residue was purified by column chromatography (230–400 mesh silica, pentane:dichloromethane:ether 10:10:0.25), to yield 147 mg Compound A7 as a white solid. (92%).

Formula: C$_{27}$H$_{28}$O$_5$

Molecular weight: 432.51

R$_f$: 0.24 (pentane:dichloromethane:ether 10:10:0.25)

Melting point: 111–112° C.

$[α]_D^{20}$=-29.5°; $[α]_{365}^{20}$=-110.1° (c=1.00 in chloroform)

IR (KBr): 2932 (m), 2885 (m), 2834 (m), 1376 (m), 1173 (m), 1142 (m), 1103 (s), 1044 (m), 1033 (m), 1008 (m), 962 (m), 828 (m), 765 (s), 749 (s), 699 (s) cm$^{-1}$

EI-MS: (m/z) 45 (18), 88 (43), 121 (100), 134 (18), 182 (31), 225 (20), 432 (2) [M$^+$]

$^1$H-NMR (500 MHz, CDCl$_3$): δ 7.78–7.68 (5H, m), 7.58–7.41 (7H, m), 5.81 (1H, s), 4.39 (1H, d, J=9.7 Hz), 4.35 (1H, dd, J=10.2, 4.9 Hz), 3.88 (1H, dd, app. t, J=10.1 Hz), 3.83 (1H, dd, app. t, J=9.2 Hz), 3.71–3.67 (1H, m), 3.69 (3H, s), 3.60 (1H, dd, app. t, J=9.1 Hz), 3.26 (1H, dd, J=9.5, 8.6 Hz), 3.11 (3H, s)

APT-NMR (125 MHz, CDCl$_3$): δ 141.4 (C), 140.6 (C), 139.6 (C), 137.4 (C), 128.9 (CH), 128.0 (CH), 127.6 (CH), 127.5 (CH), 126.9 (CH), 126.8 (CH), 126.5 (CH), 100.8

(CH), 85.4 (CH), 84.6 (CH), 82.0 (CH), 81.9 (CH), 70.5 (CH), 69.6 (CH$_2$), 59.9 (CH$_3$), 59.8 (CH$_3$)

EXAMPLE 2

Bioactivity of the Compounds of Formula A

The compounds were screened against various pathogenic viruses and more specific the human cytomegalovirus (CMV). For determination of the antiviral activity, expressed in IC$_{50}$, against 2 CMV-strains (Davis and AD-169), human embryonic lung fibroblast (HEL) cells grown in 96-well microplates were infected with 20 PFU virus/well. After 2 hours of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

The results of the screening of the new compounds against the human cytomegalovirus (CMV) are presented in Table 3.

TABLE 3

Antiviral activity of the compounds

| Compound | IC$_{50}$(µg/ml)[a] CMV | |
|---|---|---|
| | AD-169 Strain | David Strain |
| Compound A1 | 2.7 | 2.0 |
| Compound A2 | 5.0 | 20.0 |
| Compound A3 | 2.5/2.7 | 3.2/2.8 |
| Compound A4 | 0.9/1.3 | >2/1.0 |
| Compound A5 | 0.5 | 0.5 |
| Compound A6 | 0.47 | 0.8 |
| Compound A7 | 0.8 | 0.6 |
| Ganciclovir | 1.3/2.5 | 0.5 |

[a]inhibitory concentration required to reduce virus plaque formation by 50%. Virus input was 100 plaque forming units (PFU)

Each of the compounds of Formula A showed a significant activity against CMV. Activity of these new molecules (IC$_{50}$ in µg/ml) are in the same range as the activity of ganciclovir for CMV screenings.

Although the invention has been described with respect to a preferred embodiment thereof, it is to be also understood that it is not to be so limited since changes and modifications can be made therein which are within the full intended scope of this invention as defined by the appended claims.

We claim:
1. A compound of the formula:

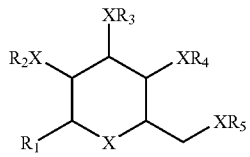

wherein:
R$_1$ is selected from the group consisting of -benzyl and -aryl;
R$_2$ and R$_3$ are selected from the group consisting of -alkyl, -aryl, -allyl and —H;
R$_4$ and R$_5$ form a ring and are selected from the group consisting of —CH(Ph)- and —CH(aryl)-;
X is selected from the group consisting of O;
or a pharmaceutically active derivative thereof.

2. A compound as defined in claim 1, wherein R$_1$ preferably is selected from the group consisting of phenyl and benzyl; R$_2$ and R$_3$ are preferably selected from the group consisting of -methyl, -ethyl, -allyl, -propargyl and hydrogen; R$_4$ and R$_5$ form a ring and are selected preferably from the group consisting of —CH(Ph)-, —CH(naphthyl)- and —CH(biphenyl)-; and X is O; or a pharmaceutically active derivative thereof.

3. A method of treating a pathogenic viral infection in a mammalian subject comprising the step of administering to the subject an effective anti-viral amount of composition comprising at least one compound of claim 1.

4. The method of claim 3 wherein the composition contains a compound of claim 1 in an effective anti-viral amount.

5. The method of claim 3 wherein the mammalian subject is a human patient or another mammal.

6. A method for treating a pathogenic viral infection in a mammalian subject where the infective agent is resistant to one or more other therapies, comprising the step of administering to the subject a composition comprising an effective anti-viral amount of a compound of claim 1.

7. A method as defined in claim 3, wherein the viral infection is an infection caused by herpesviridae.

8. A method as defined in claim 3, wherein the viral infection is an infection caused by cytomegalovirus.

* * * * *